United States Patent [19]
Chikamori et al.

[11] Patent Number: 5,929,285
[45] Date of Patent: Jul. 27, 1999

[54] METHOD FOR PRODUCING 3, 5, 5-TRIMETHYLCYCLOHEXA-3-EN-1-ONE

[75] Inventors: Masahiro Chikamori, Ibo-gun; Ikuo Takahashi, Kobe, both of Japan

[73] Assignee: Daicel Chemical Industries Ltd., Osaka, Japan

[21] Appl. No.: 08/958,371

[22] Filed: Oct. 27, 1997

[30] Foreign Application Priority Data

Nov. 15, 1996 [JP] Japan ................................. 8-304819

[51] Int. Cl.$^6$ ..................................................... C07C 49/11
[52] U.S. Cl. ................................................................ 568/372
[58] Field of Search ............................................. 568/377

[56] References Cited

U.S. PATENT DOCUMENTS 4,005,145  1/1977  Widmer .

FOREIGN PATENT DOCUMENTS 54-8650  4/1979  Japan .

*Primary Examiner*—Gary Geist
*Assistant Examiner*—Jean F Vollano
*Attorney, Agent, or Firm*—Birch, Stewart, Kolasch & Birch, LLP

[57] ABSTRACT

Highly purified 3,5,5-trimethylcyclohexa-3-en-1-one is produced with a high production efficiency by inhibiting thermal decomposition of an isomerization catalyst. The method comprises isomerizing 3,5,5-tri-methylcyclohexa-2-en-1-one (α-isophorone) in the presence of an isomerization catalyst under reduced pressure at a reaction temperature of 90° C. to 205° C., and simultaneously distilling the reaction product, thereby inhibiting thermal decomposition of the isomerization catalyst. This method provides the isomerized product at a high level of the unit-time production for a long period, and prevents contamination caused by the decomposed product of the isomerization catalyst.

13 Claims, No Drawings

5,929,285

METHOD FOR PRODUCING 3, 5, 5-TRIMETHYLCYCLOHEXA-3-EN-1-ONE

FIELD OF THE INVENTION

The present invention relates to a method for producing 3,5,5-trimethylcyclohexa-3-en-1-one (β-isophorone) from 3,5,5-trimethylcyclohexa-2-en-1-one (α-isophorone).

BACKGROUND OF THE INVENTION

Use has been made of 3,5,5-trimethylcyclohexa-3-en-1-one (β-isophorone) as a pharmaceutical or agricultural intermediate or as a material for a polymer such as polyurethane. The β-isophorone is prepared by isomerization of α-isophorone, generally in the presence of an isomerization catalyst composed of an acid.

By way of example, Japanese Patent Publication No. 8650/1979 (JP-B-54-8650) discloses a method which comprises isomerizing α-isophorone with using an acid as an isomerization catalyst and distilling the isomerized product to give β-isophorone, the acid being stable under the reaction conditions and having a pK value of 2 to 5 as well as having a higher boiling point than the isomerized product. As the isomerization catalyst, this literature uses an acid which is not thermally deformed at the isomerization temperature and which does not cause a side reaction, naming adipic acid as an example. The literature teaches that the continuous isomerization is generally conducted under atmospheric pressure, although it is also possible under reduced pressure, and that the reaction temperature should be set high in order to yield the isomerized product in as large an amount as possible per unit time. In this literature, β-isophorone is obtained in a 94% yield according to the process which comprises the steps of boiling the mixture of isophorone and the adipic acid isomerization catalyst under atmospheric pressure for isomerization, distilling the thus isomerized β-isophorone, and further rectifying the distillate under reduced pressure.

However, when the reaction is conducted under atmospheric pressure, the reaction temperature reaches 213 to 215° C., which is a boiling point of α-isophorone. At such a high temperature, the isomerization catalyst is thermally decomposed and gives a by-product. For instance, the adipic acid isomerization catalyst is thermally decomposed and by-produces cyclopentanone, water and carbon dioxide.

As a result, the amount of the isomerization catalyst (e.g. adipic acid) decreases gradually, and the isomerized product is produced in a reduced amount per unit time. For these reasons, such a process requires an additional isomerization catalyst (e.g. adipic acid) to be added into the reactor in the course of the reaction. Further, the distilled β-isophorone is contaminated, during distillation, with the by-products (cyclopentanone, etc.) resulting from the thermal decomposition.

SUMMARY OF THE INVENTION

It is, therefore, an object of the present invention to provide a method for producing β-isophorone from α-isophorone with a remarkably high efficiency for a long period, while inhibiting thermal decomposition of an isomerization catalyst and contamination by decomposed products.

It is another object of the present invention to provide a method for producing highly purified β-isophorone with maintaining the amount of its unit-time production at a high level for a prolonged period.

A further object of the present invention is to provide a method for a continuous production of highly purified β-isophorone through an isomerization reaction and distillation.

The inventors of the present invention made an intensive research to achieve the above objects and found that the isomerization reaction conducted under reduced pressure at a temperature of 90 to 205° C. provides β-isophorone for a long period with high production efficiency per unit time, with inhibiting decomposition of an isomerization catalyst and contamination by decomposed products. The present invention is based on the above findings.

The present invention is directed to a method for producing 3,5,5-trimethylcyclohexa-3-en-1-one by isomerizing 3,5,5-trimethylcyclohexa-2-en-1-one in the presence of an isomerization catalyst, wherein the object product is provided by the isomerization reaction under reduced pressure at a temperature of 90 to 205° C. As the isomerization catalysts, there may be mentioned $C_{12-24}$ higher fatty acids, aliphatic $C_{5-20}$ dicarboxylic acids, alicyclic dicarboxylic acids, aromatic carboxylic acids, and so on, such catalysts being used alone or in combination.

The method of the present invention also includes a method which comprises isomerizing 3,5,5-trimethylcyclohexa-2-en-1-one under reduced pressure at a temperature effective for preventing or inhibiting decomposition of the isomerization catalyst to give 3,5,5-trimethylcyclohexa-3-en-1-one containing (contaminated with), based on the weight, not more than 750 ppm of a decomposed by-product with a low boiling point. According to this method, 3,5,5-trimethylcyclohexa-3-en-1-one containing not more than 600 ppm, on the weight basis, of a low-boiling-point by-product can be produced by conducting isomerization under a pressure of 10 to 600 Torr at a temperature of 90 to 205° C. in the presence of the isomerization catalyst while continuously supplying 3,5,5-trimethylcyclohexa-2-en-1-one into a reactor, and continuously distilling the isomerization reaction product.

Throughout this specification, it should be understood that the phrases "a decomposed by-product having a low boiling point" and "a low-boiling-point by-product" mean a by-product which contaminates β-isophorone during isomerization and distillation. For example, when adipic acid is used as the isomerization catalyst, these phrases indicate cyclopentanone, among the decomposed by-products, not water or carbon dioxide.

DETAILED DESCRIPTION OF THE INVENTION

In this invention, β-isophorone is produced from α-isophorone through the isomerization reaction conducted in the presence of the isomerization catalyst.

The isomerization catalyst is an organic carboxylic acid which has a higher boiling point than both of α-isophorone and β-isophorone under the pressure and temperature of the isomerization reaction, where a higher boiling point than that of α-isophorone is required for the purpose of hindering reverse-isomerization. Such a catalyst (the organic acid) includes an aliphatic, alicyclic or aromatic carboxylic acid or its derivative with a boiling point of not lower than 250° C. Examples of the aliphatic carboxylic acid are a $C_{12-24}$ higher fatty acid such as hydroxystearic acid, and an aliphatic $C_{5-20}$ dicarboxylic acid such as glutaric acid, adipic acid, pimelic acid, suberic acid, azelaic acid, sebacic acid and dodecanedicarboxylic acid. The alicyclic carboxylic acid includes, for instance, an alicyclic dicarboxylic acid such as 1,4- cyclohexanedicarboxylic acid, hexahydrophthalic acid and himic acid. The aromatic carboxylic acid includes an aromatic polycarboxylic acid such as phthalic acid, isophthalic acid, 5-nitroisophthalic acid, terephthalic acid, trimellitic acid, pyromellitic acid and a naphthalenedicarboxylic acid (1,4-naphthalenedicarboxylic acid, 2,6-naphthalenedicarboxylic acid, etc.); an aromatic monocarboxylic acid or its derivative [e.g. benzoic acid derivatives (p-hydroxybenzoic acid, salicylic acid, 3-hydroxy-4-nitrobenzoic acid, 4-trifluoromethylbenzoic acid, 3,4,5-trimethoxybenzoic acid, 3,4,5-trimethylbenzoic acid, vanillic acid, etc.), naphthoic acid, toluic acid or its derivatives (p-toluic acid, 4-nitro-3-toluic acid, etc.)]; a phenylphosphinic acid; an indolecarboxylic acid; and the like. These isomerization catalysts can be used independently or as a mixture of two or more species.

Preferred isomerization catalysts include an aliphatic saturated $C_{6-12}$ dicarboxylic acid (particularly, an aliphatic $C_{6-10}$ dicarboxylic acid such as adipic acid), and an aromatic polycarboxylic acid [e.g. aromatic dicarboxylic acids including isophthalic acid, terephthalic acid and a naphthalenedicarboxylic acid (1.4-naphthalenedicarboxylic acid, 2,6-naphthalenedicarboxylic acid, etc.)]. Adipic acid is particularly preferable.

The amount of the isomerization catalyst can be selected in a range not sacrificing the isomerization efficiency. For instance, the amount of the catalyst is about 1 to 15% by weight (e.g. 1 to 12% by weight), preferably about 3 to 10% by weight, and more preferably about 5 to 10% by weight (e.g. 5 to 8% by weight), relative to the amount of α-isophorone.

A feature of the present invention is to produce β-isophorone from α-isophorone with high efficiency through the isomerization reaction under reduced pressure at a specific temperature, so as to protect the isomerization catalyst from decomposition or deterioration and to prevent contamination of the object product due to the decomposed product. Above all, highly purified β-isophorone can be continuously provided for a long period in good yield and in a large amount by conducting, under reduced pressure, isomerization of α-isophorone side by side with separation and purification of the isomerized product by distillation or rectification (vacuum distillation or rectification).

The isomerization reaction is effected at a temperature at which decomposition of the isomerization catalyst can be inhibited, for example, at about 90 to 205° C. (e.g. 90 to 200° C.), preferably about 120 to 195° C., and more preferably about 140 to 190° C. The reaction pressure is a pressure suitable for inhibiting decomposition of the isomerization catalyst, determined in accordance with the reaction temperature. Generally, the reaction pressure is about 10 to 600 Torr, preferably about 50 to 550 Torr, and more preferably about 100 to 500 Torr. Under these conditions, the isomerization reaction ensures an efficient production of highly purified β-isophorone, with inhibiting decomposition of the isomerization catalyst. The temperature and pressure for the reaction can be liberally selected, in a range not exceeding the boiling point of the isomerization catalyst, as far as the combination can ensure a high isomerization efficiency and inhibition of by-product production. In a desirable embodiment, contamination of β-isophorone by the low-boiling-point by-product is avoided during the isomerization reaction, by preventing decomposition of the isomerization catalyst as well as maintaining the amount of the decomposed by-product with a low boiling point at about 750 ppm or less (e.g. 0 to 700 ppm), preferably about 600 ppm or less (e.g. 0 to 500 ppm), on the weight basis.

The isomerization reaction can be conducted in a batch system, a semi-batch system or a continuous system. Continuous operation is preferable among them.

The isomerization reaction product is separated and purified by a conventional process to give β-isophorone, separation and purification means including separation means such as filtration, concentration, distillation, extraction, crystallization, recrystallization, and column chromatography; and combined separation means thereof. In the present invention, β-isophorone can be separated and purified on an industrial basis by a conventional distillation or rectification process using a distilling column (or a rectifying column), because, according to the present invention, β-isophorone is significantly protected from contamination with the decomposed products by inhibiting decomposition of the isomerization catalyst.

The distilling column (or tower) may be either a packed column (or tower) or a plate column (or tower). The number of column plates or trays in the distilling column is not strictly specified, and is usually about 20 or more (e.g. 20 to 70), and preferably about 25 to 50 (e.g. 30 to 50). For the distillation, the temperature at the top of the column is at about 80 to 180° C., preferably about 100 to 180° C., and more preferably about 120 to 175° C. The distillation operation can be conducted in a conventional manner, for example, by condensing the vapour from the top of the column and withdrawing a portion of the condensed liquid out of the reaction system with refluxing the condensed liquid (condensate). One or plural distilling tower(s) can be employed for the distillation.

Although the distillation process may be batch distillation, continuous distillation is advantageous in terms of industrial applicability.

In the method of the present invention, it is possible to conduct the isomerization step and the separation step (the distillation step) separately. However, a desirable embodiment is carried out by isomerizing α-isophorone, with continuous addition thereof into the reactor, in the presence of the isomerization catalyst under the above-specified conditions, and by continuously distilling the isomerization reaction product, whereby the isomerization reaction, and the separation and purification (distillation) proceed continuously in parallel. In the course of such a process, the isomerization reaction usually progresses side by side with the distillation, while the liquid level of the mixture of α-isophorone and the isomerization catalyst being adjusted or maintained roughly at a predetermined level (a fixed level). A proper combination of the above-specified reaction conditions with the process of synchronised isomerization and distillation contributes to the production of highly purified β-isophorone in a dramatically improved amount per unit time.

The product of the present invention, β-isophorone, can be used as a pharmaceutical or agricultural intermediate product, or as a material for polymers such as polyurethane, polyester and polyamide.

The present invention, according to which the isomerization reaction is performed under specific conditions, inhibits thermal decomposition of the isomerization catalyst, remarkably reduces the amount of further addition thereof during the reaction, and prevents the reaction product from contamination by the decomposed product. As a consequence, β-isophorone is produced from α-isophorone for a prolonged period of time with drastically high efficiency. The present invention shows excellent productivity of β-isophorone, thus being remarkably advantageous in industrial and economic points of view. Moreover, the present invention provides highly purified β-isophorone, with maintaining the amount of its unit-time production at a high level for a long time. Further, the combination of the isomerization reaction with the distillation step serves to strongly prevent β-isophorone from being contaminated with the decomposed product of the isomerization catalyst, ensuring a continuous production of highly purified β-isophorone without any complicated distillation process.

The following examples are intended to describe the present invention in further detail and should by no means be interpreted as defining the scope of the invention.

EXAMPLES

Example 1

In a flask (capacity: 1 liter; connected to a plate column) were fed 3,5,5-trimethylcyclohexa-2-en-1-one (553 g) and adipic acid (38 g). Isomerization was carried out under a pressure of 340 Torr with a temperature (liquid phase) of 190° C. in the flask, while controlling the charge (supply) of 3,5,5-trimethylcyclohexa-2-en-1-one to keep the temperature at 154° C. at the top of the column, and simultaneously, continuous distillation was effected using a distilling column "Order show" equipped with 30 plates, adjusting the liquid level in the flask at a predetermined level. As a result, 3,5,5-trimethylcyclohexa-3-en-1-one was constantly obtained from the top of the column in 25 g per hour, its concentration being 99% or higher (analysed by gas chromatography).

By continuously conducting the above operation, the production amount of 3,5,5-trimethylcyclohexa-3-en-1-one reached 25.03 kg after 1,000 hours (yield based on the charged 3,5,5-trimethylcyclohexa-2-en-1-one: 97%). No cyclopentanone was detected by gas chromatography.

Example 2

The procedure of Example 1 was repeated under a pressure of 460 Torr and a flask liquid temperature of 200° C., with controlling the charge of 3,5,5-trimethylcyclohexa-2-en-1-one to keep the temperature at the top of the column at 166° C. This process provided, from the top of the column, 3,5,5-trimethylcyclohexa-3-en-1-one, with a concentration of 99% or higher, in 20 g per hour on the average.

After 1,000 hours, the thus obtained 3,5,5-trimethylcyclohexa-3-en-1-one amounted to 20.02 kg (yield based on the charged 3,5,5-trimethylcyclohexa-2-en-1-one: 97%). By means of gas chromatography, 500 ppm of cyclopentanone was observed on the weight basis.

Comparative Example 1

The procedure of Example 1 was repeated under atmospheric pressure at a flask liquid temperature of 220° C., with controlling the charge of 3,5,5-trimethylcyclohexa-2-en-1-one to keep the temperature at the top of the column at 184° C. Consequently, 3,5,5-trimethylcyclohexa-3-en-1-one was obtained from the top of the column in an average amount of 10 g per hour, its concentration being 99% or higher.

The amount of 3,5,5-trimethylcyclohexa-3-en-1-one obtained after 1,000 hours was 10.01 kg (yield based on the charged 3,5,5-trimethylcyclohexa-2-en-1-one: 97%), in which 2,000 ppm (on the weight basis) of cyclopentanone was observed by gas chromatography.

By comparing the results of Examples and Comparative Example, it is apparent that the methods of the above Examples can produce 3,5,5-trimethylcyclohexa-3-en-1-one with remarkably high purity, and its production efficiency is, at least, twice as high as that of Comparative Example.

What is claimed is:

1. A method for producing 3,5,5-trimethylcyclohex-3-en-1-one by isomerization of 3,5,5-trimethylcyclohex-2-en-1-one in the presence of an isomerization catalyst, which method comprises isomerizing, 3,5,5-trimethylcyclohex-2-en-1-one under a pressure of 10 to 600 Torr at a reaction temperature of 90 to 205° C. to distill the isomerization reaction product which contains a decomposed by-product in not more than 750 ppm.

2. A method for producing 3,5,5-trimethylcyclohex-3-en-1-one as claimed in claim 1, wherein said isomerization catalyst is at least one member selected from the group consisting of $C_{12-24}$ higher fatty acids, aliphatic $C_{5-20}$ dicarboxylic acids, alicyclic dicarboxylic acids and aromatic carboxylic acids.

3. A method for producing 3,5,5-trimethylcyclohex-3-en-1-one as claimed in claim 1, wherein said isomerization catalyst is at least one member selected from the group consisting of aliphatic $C_{6-12}$ dicarboxylic acids and aromatic polycarboxylic acids.

4. A method for producing 3,5,5-trimethylcyclohex-3-en-1-one as claimed in claim 1, wherein said isomerization catalyst is at least one member selected from the group consisting of adipic acid, isophthalic acid, terephthalic acid and a naphthalenedicarboxylic acid.

5. A method for producing 3,5,5-trimethylcyclohex-3-en-1-one as claimed in claim 1, which comprises:

continuously supplying 3,5,5-trimethylcyclohex-2-en-1-one in a reactor and isomerizing it in the presence of the isomerization catalyst under a pressure of 10 to 600 Torr at a reaction temperature of 90 to 205° C., and continuously distilling the isomerization reaction product, in parallel with said isomerization, thereby producing 3,5,5-trimethylcyclohex-3-en-1-one which contains a decomposed by-product having a low boiling point in not more than 600 ppm on the weight basis.

6. A method for producing 3,5,5-trimethylcyclohex-3-en-1-one as claimed in claim 5, wherein said isomerization catalyst is at least one member selected from the group consisting of aliphatic $C_{6-12}$ dicarboxylic acids and aromatic polycarboxylic acids; has a boiling point of not lower than 250° C.; and is used in a proportion of 1 to 15% by weight relative to 3,5,5-trimethylcyclohex-2-en-1-one.

7. A method for producing 3,5,5-trimethylcyclohex-3-en-1-one as claimed in claim 1, wherein said isomerization is performed at a reaction temperature of 90 to 200° C.

8. A method for producing 3,5,5-trimethylcyclohex-3-en-1-one as claimed in claim 1, wherein said isomerization is performed at a reaction temperature of 120 to 195° C.

9. A method for producing 3,5,5-trimethylcyclohex-3-en-1-one as claimed in claim 1, wherein said isomerization is performed at a reaction temperature of 140 to 190° C.

10. A method for producing 3,5,5-trimethylcyclohex-3-en-1-one as claimed in claim 1, wherein said isomerization is performed at a pressure of 50 to 550 torr.

11. A method for producing 3,5,5-trimethylcyclohex-3-en-1-one as claimed in claim 1, wherein said isomerization is performed at a pressure of 100 to 500 torr.

12. A method for producing 3,5,5-trimethylcyclohex-3-en-1-one as claimed in claim 1, wherein said isomerization is performed at a pressure of 50 to 550 torr and at a reaction temperature of 120 to 195° C.

13. A method for producing 3,5,5-trimethylcyclohex-3-en-1-one as claimed in claim 1, wherein said isomerization is performed at a pressure of 100 to 500 torr and at a reaction temperature of 140 to 190° C.

* * * * *